United States Patent [19]

Dupuis

[11] Patent Number: 5,900,229
[45] Date of Patent: * May 4, 1999

[54] USE OF A VINYL LACTAM-DERIVED TERPOLYMER AS A FOAMING AGENT IN COMPOSITIONS FORMING AN AEROSOL FOAM

[75] Inventor: Christine Dupuis, Paris, France

[73] Assignee: L'Oreal, Paris, France

[ * ] Notice: This patent issued on a continued prosecution application filed under 37 CFR 1.53(d), and is subject to the twenty year patent term provisions of 35 U.S.C. 154(a)(2).

[21] Appl. No.: 08/367,304
[22] PCT Filed: May 2, 1994
[86] PCT No.: PCT/FR94/00499
§ 371 Date: Jan. 5, 1995
§ 102(e) Date: Jan. 5, 1995
[87] PCT Pub. No.: WO94/26238
PCT Pub. Date: Nov. 24, 1994

[30] Foreign Application Priority Data

May 7, 1993 [FR] France .................................. 93 05523

[51] Int. Cl.$^6$ ...................................................... A61K 9/12
[52] U.S. Cl. ........................ 424/47; 424/45; 424/DIG. 1; 424/DIG. 2; 424/70.11; 424/78.02; 424/70.15; 424/70.16; 424/70.9; 514/957; 514/945; 132/202
[58] Field of Search .......................... 424/45, 47, DIG. 1, 424/DIG. 2, 70.11, 78.02, 70.15, 70.16, 70.9; 514/957, 945; 132/202

[56] References Cited

U.S. PATENT DOCUMENTS

| | | | |
|---|---|---|---|
| 3,405,084 | 10/1968 | Bohac et al. ............................ | 260/29.6 |
| 4,300,580 | 11/1981 | O'Neill et al. ...................... | 424/DIG. 1 |
| 4,876,083 | 10/1989 | Grollier et al. ............................ | 424/47 |
| 4,897,262 | 1/1990 | Nandagiri et al. .................... | 424/70.11 |
| 5,015,708 | 5/1991 | Shih et al. ............................... | 526/264 |
| 5,164,177 | 11/1992 | Bhatt et al. ............................... | 424/47 |
| 5,266,303 | 11/1993 | Myers et al. ............................... | 424/47 |
| 5,620,684 | 4/1997 | Dupuis ................................. | 424/70.12 |
| 5,830,438 | 11/1998 | Dupuis ..................................... | 424/45 |

FOREIGN PATENT DOCUMENTS

| | | |
|---|---|---|
| 0 523 388 | 1/1993 | European Pat. Off. . |
| 2679444 | 1/1993 | France . |
| 2106595 | 10/1970 | Germany . |
| 2109522 | 9/1972 | Germany . |

OTHER PUBLICATIONS

Oteri, R. et al. (1991). Cosmetics & Toiletries vol. 106 (Jul. issue), pp. 30–34.

Primary Examiner—Raj Bawa
Attorney, Agent, or Firm—Jacobson, Price, Holman & Stern, PLLC

[57] ABSTRACT

The invention relates to the use as sole or additional foaming agent in aqueous compositions for treating the skin or the hair, which are packaged in an aerosol device and are capable of forming a foam after expansion into the air, of a terpolymer consisting of 25 to 90% of vinyl lactam, of 1 to 55% of unsaturated carboxylic acid and of 1 to 20% of alkyl acrylate or methacrylate containing at least 6 carbon atoms, and to cosmetic or dermatological compositions packaged as an aerosol and forming a foam in the air, containing the terpolymer.

24 Claims, No Drawings

USE OF A VINYL LACTAM-DERIVED TERPOLYMER AS A FOAMING AGENT IN COMPOSITIONS FORMING AN AEROSOL FOAM

The present invention relates to the use of a vinyl lactam-derived terpolymer in compositions intended for treating the hair and/or the skin, which compositions are pressurized as an aerosol and form a foam at the outlet of the aerosol device.

Cosmetic compositions which are pressurized in aerosol devices, under conditions such that they form a foam at the outlet, are well known and are used especially in treating the hair and/or the skin.

Such compositions will be referred to as "aerosol foam" in the remainder of the description.

These foams generally make it possible to obtain good spreading of the cosmetic compositions on the hair and, in addition, they are easy to use and are more economical in terms of the products.

These foams should be sufficiently stable so as not to be liquefied rapidly and should also disappear rapidly when massaged in, which serves to make the composition penetrate into the hair or to spread the former over the skin.

Anionic, nonionic or amphoteric surface-active agents may be used to form foams but, when used alone, these surface agents produce foams of unsatisfactory quality, insofar as are [sic] they liquefy at the time of application or they do not disappear after application at the time of massaging in.

Another means of forming foams is to use foaming polymers, but, in this case, difficulties of solubilizing the polymers in water are encountered or, if these polymers are sufficiently soluble, the cosmetic properties of the resulting foams can be further enhanced.

The Applicant has discovered that the use of a terpolymer consisting of:

25 to 90% of vinyl lactam,
1 to 55% of unsaturated carboxylic acid,
1 to 20% of alkyl (meth)acrylate, containing at least 6 carbon atoms, made it possible to obtain a foam which imparts holding of the style to the hair (shape-retention of the hairstyle) and imparts softness to the hair. The foam thus obtained also imparts enhanced softness to the skin.

The foams obtained in accordance with the invention are particularly stable and rigid for their use in the cosmetic treatment of the skin and of the hair, they possess film-forming properties and are particularly advantageous in terms of the softness which they impart to the hair and to the skin.

These foams also constitute a particularly suitable vehicle for applying cosmetic or dermatological active agents to the skin or to the hair.

A "cosmetic treatment" will refer in the remainder of the description to any treatment which aims to enhance the surface condition or esthetics of the skin or of the hair.

"Dermatological treatment" will refer to a treatment using active substances having a therapeutic or preventive effect towards a skin disease.

The subject of the invention is thus the use as foaming agent of a vinyl lactam-derived copolymer defined below.

Another subject of the invention consists of the cosmetic compositions intended for treating the skin or the hair, which are applied in the form of a foam from an aerosol device for treating the skin or the hair.

A further subject of the invention is a process for treating the skin and the hair which uses such a foam.

Other subjects of the invention will become apparent on reading the description and the examples which follow.

The copolymer used as foaming agent in the compositions intended to be applied to the skin or to the hair, in order to form a foam from a composition which is packaged in an aerosol device, is a terpolymer consisting of:

25 to 90% of vinyl lactam,
1 to 55% of unsaturated carboxylic acid
1 to 20% of an alkyl (meth)acrylate containing at least 6 carbon atoms.

The vinyl lactam is in particular 2-vinylpyrrolidone.

The unsaturated carboxylic acid is preferably chosen from acrylic acid, methacrylic acid, itaconic acid or crotonic acid.

The alkyl acrylate or methacrylate containing at least 6 carbon atoms is preferably an acrylic or methacrylic ester containing from 8 to 18 carbon atoms.

The alkyl groups are preferably chosen from 2-ethylhexyl, octyl, lauryl and stearyl groups.

The polymers which may be used in accordance with the invention are known per se and may be prepared, for example, according to the process described in U.S. Pat. No. 5,015,708.

The terpolymers which may be used in accordance with the invention are preferably chosen from polymers containing:

40 to 70% of vinylpyrrolidone,
15 to 40% of unsaturated carboxylic acid, and
5 to 20% of alkyl (meth)acrylate, having a number of carbon atoms between 8 and 18.

The particularly preferred copolymers are chosen from the terpolymers of vinylpyrrolidone, of (meth)acrylic acid and preferably of acrylic acid and of lauryl methacrylate.

The polymer marketed under the name "ANIONIC VP TERPOLYMER" by the company ISP, comprising 66 to 68% by weight of vinylpyrrolidone, 23 to 25% of acrylic acid and 9% of lauryl methacrylate, is a particularly preferred polymer.

The terpolymer used in accordance with the invention is used as sole or additional foaming agent.

The polymer is referred to as the sole foaming agent when it is used alone to form the foam; it will be considered as being involved as an additional foaming agent when it is used in conjunction with other compounds capable of foaming.

By virtue of the use of the terpolymer defined above, the foam obtained after expansion into the open air from the aerosol device has a density of less than or equal to 0.3 $g/cm^3$ at 20° C.

The density is determined in the following way:

A 1% aqueous solution of terpolymer is packaged in an aerosol can consisting of a one-piece aluminum can of (45×28) with a valve, precision P73, containing no plunger tube and having an axial push-button diffuser for a conical cupola, 021550. The aerosol can is filled with an amount of 90 g of 1% terpolymer solution and 10 g of AEROGAZ 3.2N propellent gas consisting of butane, isobutane >55% and propane, sold by the company ELF AQUITAINE. The operation is carried out 24 hours after pressurization of the aerosol in a conditioned room at 20° C.±1° C. The equipment and the sample are at the same temperature. A small cylindrical cup is weighed while empty (which gives its weight P1) and then immediately filled with the foam produced by the aerosol. Each aerosol can is shaken well before use in order to emulsify the propellent gas.

For uniform distribution of the foam in the cup, the aerosols are used upside-down in a smooth rotating motion.

As soon as the expansion of the foam has stopped, it is immediately and rapidly leveled off using a wide spatula and the cup is weighed again, which gives its weight P2.

The density of the foam is determined according to the following formula:

$$\text{density at } 20° \text{ C.} = P2 - P1/V$$

(V is the volume of the cup).

Three determinations are made for each polymer. The value adopted is the average value of these determinations in g/cm$^3$.

The foam obtained by virtue of the use of the terpolymer in accordance with the invention furthermore exhibits particularly enhanced stability, of greater than 5 minutes.

The foam stability is measured by introducing into a 50 ml measuring cylinder 5 g of foam obtained from an aqueous 1% polymer solution, which has been packaged as described above, followed by measuring the amount of time taken for the foam to become liquefied giving 5 ml of liquid.

The foam obtained in accordance with the invention is particularly rigid, that is to say that it does not liquefy at the time of application to the hair or to the skin, but disappears rapidly on massaging in. This disappearing time is generally between 10 and 40 seconds.

The vinyl lactam-based terpolymer as defined above is generally used in a cosmetically acceptable medium which is suitable for application to the hair or to the skin. The terpolymer is present in this medium in proportions of between 0.05 and 10% by weight relative to the total weight of the composition, and preferably between 0.2 and 3%.

The composition introduced into the aerosol device and which, after expansion, forms the aerosol foam constitutes another subject of the invention. It is characterized in that it contains, in the abovementioned proportions, the vinyl lactam-based terpolymer as defined above, in a cosmetically acceptable aqueous medium and in proportions which are sufficient to form a rigid and stable foam after expansion into the air from the aerosol device.

The aqueous cosmetic media may contain, in addition to water, any cosmetically acceptable solvent chosen in particular from monoalcohols, for instance alkanols having from 1 to 8 carbon atoms such as ethanol, isopropanol, benzyl alcohol and phenethyl alcohol; polyalcohols, for instance alkylene glycols such as ethylene glycol; glycol ethers such as mono-, di- and triethylene glycol; alkyl ethers such as, for example, ethylene glycol monomethyl ether, ethylene glycol monoethyl ether and diethylene glycol monoethyl ether, which are used alone or as a mixture.

These solvents, when they are present, are used in proportions of less than or equal to 50% by weight, and preferably of less than 30% by weight, relative to the total weight of the composition, and in such amounts as to make it possible to obtain, with the vinyl lactam-derived terpolymer defined above, a foam having a density of less than or equal to 0.3 g/cm$^3$ at 20° C. and a stability of greater than 5 minutes, in this cosmetically acceptable medium.

The compositions in accordance with the invention may contain agents for the cosmetic treatment of the hair and/or of the skin, or dermatologically active substances.

These agents for the cosmetic treatment of the hair and/or of the skin may or may not have foaming properties when they are used alone in the cosmetic medium not containing the vinyl lactam-derived terpolymer as defined above.

A cosmetic agent is considered not to foam when it does not form a foam or when the density of the aerosol foam is greater than 0.3 g/cm$^3$ at 20° C., according to the test described above for the vinyl lactam-derived terpolymer.

The cosmetically active agents may be products whose aim is to enhance the sheen, the feel, the disentangling or the hold, to provide an anti-greasy or anti-dandruff effect or alternatively to strengthen, reshape or condition the hair.

Among these cosmetically active agents there may be mentioned cationic treating agents, consisting of surface-active agents or of polymers.

Among these compounds, there may more particularly be mentioned:

fatty amine derivatives such as alkyl ($C_{12}$–$C_{20}$) amidopropyldimethylamines;

salts such as alkylamine acetates, quaternary ammonium salts such as alkyldimethylhydroxyethylammonium chlorides, bromides or hydrogen phosphates, acetyldimethyldodecylammonium chloride, alkylamidoethyltrimethylammonium methosulfates, lactates of N,N-di-methylamino- or N,N-diethylaminopolyoxyethylcarboxylate which is oxyethylenated, for example, with 4 moles of ethylene oxide, alkylpyridinium salts such as 1-(2-hydroxyethyl)carbamoylmethylpyri-dinium chloride and N-lauryl, colaminoformylmethylpyridinium [sic] chloride, and imidazoline derivatives such as alkylimidazolines;

amine oxides, alkyldimethylamine oxides, alkylaminoethyldimethylamine oxides and alkylamidopropyldimethylamine oxides.

The cationic derivatives corresponding to the formula:

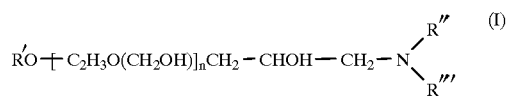

in which:

R' denotes a saturated or unsaturated linear or branched alkyl radical or an alkylaryl radical having a linear or branched alkyl chain, containing from 8 to 22 carbon atoms;

R" and R'" denote lower hydroxyalkyl radicals or alkylene radicals which are joined together to form a heterocycle;

n is a number between 0.5 and 10.

Other cationic surface agents which may be used are the water-dispersible compounds of formula (II):

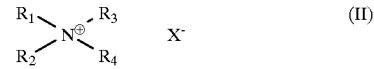

in which:

a) When $R_1$ denotes the group of formula:

in which:

$R_5$ denotes a saturated or unsaturated linear or branched aliphatic radical;

$R_6$ is an alkyl radical, a linear or branched alkoxymethyl radical or a linear alkenyloxy radical;

p denotes an integer or decimal fraction from 1 to 2.5;

n denotes an integer or decimal fraction from 2 to 20;

$R_2$ denotes an alkyl or hydroxyalkyl radical having from 1 to 3 carbon atoms;

$R_3$ and $R_4$, which may be identical or different, denote an alkyl or hydroxyalkyl radical having from 1 to 3 carbon atoms or alternatively form, with the nitrogen atom to which they are attached, a 5- or 6-membered heterocycle;

X⁻ denotes an anion and preferably a methylsulfate, methanesulfonate, p-toluenesulfonate, bromide, chloride or iodide anion.

b) When $R_2$ and $R_3$ denote a methyl radical;
$R_1$ and $R_4$ have the following meanings:
(i) $R_1$ and $R_4$ denote a linear aliphatic radical;
(ii) or alternatively $R_1$ denotes a saturated linear aliphatic radical and $R_4$ denotes a methyl, hydroxyethyl or benzyl radical or a panthenol residue;
(iii) or alternatively $R_1$ denotes an alkylamidopropyl radical ($C_{14}$–$C_{22}$ for the alkyl) and $R_4$ denotes an alkylacetate group ($C_{12}$–$C_{16}$ for the alkyl).

X⁻ denotes an anion such as a halide or $CH_3SO_4^-$.

c) When $R_1$ denotes an alkylamidoethyl and/or alkenylamidoethyl group, in which the alkyl and/or alkenyl radical containing from 14 to 22 carbon atoms is derived from tallow fatty acids and $R_2$ and $R_3$ form with the nitrogen a substituted heterocycle of the 4,5-dihydroimidazole type;
$R_4$ denotes a $C_1$–$C_4$ alkyl;
X⁻ denotes a $CH_3SO_4^-$ anion.

The bis-quaternary ammonium derivatives containing two lipophilic chains, chosen from:
a) those of formula:

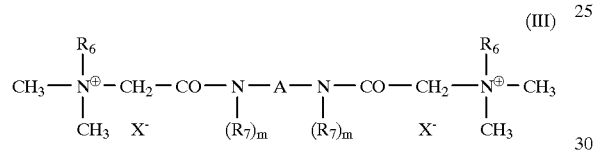

in which:
$R_6$ denotes a saturated or unsaturated linear or branched aliphatic group having from 8 to 22 carbon atoms or the mixture of these groups or a mixture of lipophilic chains derived from natural products, having from 8 to 30 carbon atoms;
A denotes a group —$(CH_2)_n$—, in which n denotes an integer from 1 to 18;
$R_7$ denotes H; and
m=1;
A may also form, with the nitrogen atoms to which it is attached, a heterocyclic group, in which case m=0;
X⁻ denotes an anion derived from an inorganic or organic acid.

These compounds are described in French Patent No. 2,464,710 of the Applicant.

b) α,ω-bis ($C_{16}$–$C_{18}$ alkyldimethylammonio) hydroxyalkylenes.

Among the more particularly preferred cationic surface-active agents there may be mentioned:
(1) the compounds of formula:

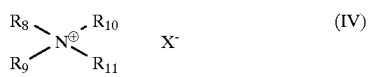

in which:
$R_8$ and $R_{11}$ each denote $C_{16}$–$C_{18}$ alkyl radicals or a mixture of alkenyl and/or alkyl radicals derived from tallow fatty acids, having 14 to 22 carbon atoms; and
$R_9$ and $R_{10}$ denote the methyl radical;
X⁻ denotes the Cl⁻ ion;
or alternatively $R_8$ denotes a $C_{18}$ alkyl radical or a panthenol residue, $R_{11}$ denotes a benzyl radical, $R_9$ and $R_{10}$ denote the methyl radical and X⁻ denotes Cl⁻.

(2) bis-quaternary ammonium derivatives bearing an ester group, such as the product sold under the name "AMONYL DM" by the company SEPPIC.

(3) the bis-quaternary ammonium derivative corresponding to the formula:

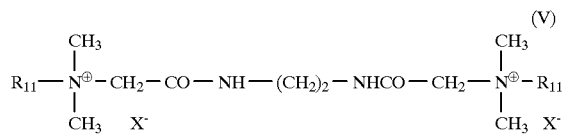

in which $R_{11}$ is a tallow chain and X⁻ is Cl⁻.

(4) alkyl (tallow) trimethylammonium chloride, sold as a solution in isopropyl alcohol under the name "ARQUAT T 50" by the company ARMAK, cetyltrimethylammonium chloride or bromide, and myristyltrimethylammonium bromide.

(5) 2-hydroxy-1,3-bis(stearyldimethylammonium) propane, sold as an aqueous-alcoholic solution under the name "M. QUAT. DIMER 18" by the company MAZER CHEMICALS.

(6) 1-methyl-2-alkyl-3-alkylamidoethylimidazolinium methosulfate, in which the alkyl group is derived from tallow fatty acids, sold under the name "REWOQUAT W 7500" by the company REWO.

(7) cocoylamidopropyldimethylacetamidoammonium chloride, corresponding to the formula:

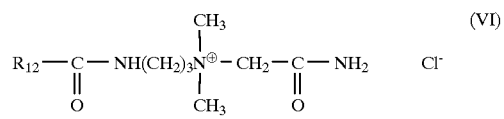

where the radical $R_{12}$ is a coconut-derived chain.

(8) acylamidopropyldimethylethylammonium ethylsulfate, in which the acyl group is derived from lanolin fatty acids, sold under the name "LANOQUAT 50" and referenced under the name QUATERNIUM 33 in the CTFA dictionary.

(9) γ-gluconamidopropyldimethylhydroxyethylammonium chloride, sold under the name "CERAPHYL 60" by the company VAN DYK and referenced under the name QUATERNIUM 22 in the CTFA dictionary.

(10) trimethyldocosylammonium chloride.

(11) cetyldimethyl(2'-hydroxyethyl)ammonium phosphate, sold under the name "LUVIQUAT MONO cp" by the company BASF.

(12) stearyldimethylamine oxide and alkyl(coco) amidopropyldimethylamine oxide.

(13) stearylamidopropyldimethylamine.

As cosmetic active agent, it is also possible to use cationic polymers which are chosen from polymers containing primary, secondary, tertiary and/or quaternary amine groups, forming part of the polymer chain or directly attached thereto by way of a hydrocarbon group having a molecular weight between 500 and approximately 5,000,000, and preferably between 1,000 and 3,000,000.

Among these polymers, quaternized proteins, quaternized polysiloxanes and polymers of the polyamine, polyaminoamide and quaternary polyammonium type may be mentioned more particularly.

A. The quaternized proteins are, in particular, chemically modified polypeptides bearing quaternary ammonium groups at the end of the chain or grafted onto the latter.

B. The silicone-containing cationic polymers constitute another family of cationic polymers. These silicone-containing cationic polymers are polydimethylsiloxanes or polydiphenylsiloxanes or alternatively polymethylphenylsiloxanes containing, at least pendant or at the end of the chain, one hydrocarbon chain which is interrupted by one or more amino groups.

C. The polymers of the polyamine, polyaminoamide or quaternary polyammonium type which may be used in accordance with the present invention are described in particular in French Patents No. 82 07 996 or 84 04 475 of the Applicant.

Among these polymers, there may be mentioned:

(1) Vinylpyrrolidone-dialkylaminoalkyl acrylate or methacrylate copolymers, which may or may not be quaternized, such as the products sold under the name "GAFQUAT" by the company GAF CORPORATION such as, for example, "GAFQUAT 734 or 735", or alternatively the products entitled "COPOLYMER 845, 958 and 937". These polymers are described in detail in French Patent 2,077,143 and 2,393,573. Mention is also made of GAFFIX VC-713, sold by the company GAF, which is a vinylcaprolactam/vinylpyrrolidone/dimethylaminoethyl methacrylate copolymer.

(2) Cellulose ether derivatives containing quaternary ammonium groups, described in French Patent 1,492,597, and in particular the polymers marketed under the names "JR" (JR 400, JR 125, JR 30M) or "LR" (LR 400, LR 30M) by the company UNION CARBIDE CORPORATION. The polymers are also defined in the CTFA dictionary as hydroxyethylcellulose quaternary ammoniums which have reacted with an epoxide which is substituted with a trimethylammonium group.

(3) Cationic cellulose derivatives such as the cellulose copolymers or the cellulose derivatives which are grafted with a water-soluble quaternary ammonium monomer and which are described in greater detail in U.S. Pat. No. 4,131,576, such as hydroxyalkylcelluloses, for instance the hydroxymethyl-, hydroxyethyl- or hydroxypropylcelluloses grafted with a methacryloyloxyethyltrimethylammonium, methacrylamidopropyltrimethylammonium or dimethyldiallylammonium salt.

The commercial products corresponding to this definition are more particularly the products sold under the names "CELQUAT L 200" and "CELQUAT H 100" by the company NATIONAL STARCH.

(4) Polymers consisting of piperazinyl units and of divalent alkylene or hydroxyalkylene radicals containing straight or branched chains, which are optionally interrupted with oxygen, sulfur or nitrogen atoms or with aromatic or heterocyclic rings, as well as the oxidation and/or quaternization products of these polymers. Such polymers are described in French Patents 2,162,025 and 2,280,361.

(5) Water-soluble polyaminoamides prepared in particular by polycondensation of an acidic compound with a polyamine. These polyaminoamides may optionally be crosslinked and/or alkylated. Such polymers are described in particular in French Patents 2,252,840, 2,368,508 and 1,583, 363, as well as in U.S. Pat. No. 3,227,615 and 2,961,347.

Other cationic polymers which may be used in accordance with the invention are chitin derivatives, for instance the quaternary derivative LEXQUAT.CH, sold by the company INOLEX, which is the product of reacting chitosan and propylene oxide, quaternized with epichlorohydrin, and the cationic derivative KYTAMER PC, sold by the company AMERCHOL, which is chitosan pyrrolidonecarboxylate.

The treating agents may also be of anionic nature and more particularly anionic polymers used alone or in combination with the cationic treating agents defined above.

A particularly preferred embodiment consists in using cationic polymers and anionic polymers in combination, as described in French Patents 2,542,997, 2,544,000, 2,521,427 and 2,383,660.

The anionic polymers contain carboxylic acid, sulfonic acid or phosphoric acid units and have a molecular weight between 500 and 5,000,000, and preferably between 1,000 and 3,000,000.

Among these polymers, there may more particularly be mentioned:

the alkali metal salts of polyhydroxycarboxylic acids, such as the products sold under the name "HYDAGEN F" by the company HENKEL;

the homopolymers, preferably non-crosslinked, of acrylic acid or methacrylic acid or the salts thereof, such as, for example, the products sold under the names "VERSICOL E or K" by the company ALLIED COLLOID, or the product sold under the name "DARVAN No. 7" by the company VAN DER BILT;

methacrylic acid/$C_1$–$C_4$ alkyl methacrylate copolymers;

the copolymers derived from maleic, fumaric and itaconic acids or anhydrides and from vinyl esters, from vinyl ethers, from vinyl halides, from phenylvinyl derivatives, from acrylic acids or from acrylates, these copolymers optionally being partially or totally esterified and described more particularly in U.S. Pat. Nos. 2,047,398, 2,723,248 and 2,102,213 and in British Patent 839,805. Among these copolymers, there may more particularly be mentioned the products sold under the names "GANTREZ" "AN or ES" by the company GENERAL ANILINE or "EMA 1325" by the company MONSANTO. Other polymers belonging to this class are copolymers of maleic, fumaric or itaconic anhydride and of an allylic or methallylic ester, and optionally of acrylamide, of methacrylamide, of an alpha-olefin, of acrylic or methacrylic acid or the esters thereof or of vinylpyrrolidone; the anhydride functions being monoesterified or monoamidated as described in the published French Patent Applications 76 13 929 and 76 20 917;

terpolymers consisting of 10 to 91% by weight of vinyl acetate, of 3 to 20% by weight of an unsaturated carboxylic acid preferably chosen from crotonic acid, allyloxyacetic acid, allyloxypropionic acid and vinylacetic acid and of 4 to 60% by weight of at least one vinyl, allyl or methallyl ester of an alpha-cyclic carboxylic acid. Among these polymers, there may preferably be mentioned the vinyl acetate/crotonic acid/vinyl t-butylbenzoate (65/10/25) copolymer as described in French Patent No. 2,439,798;

vinyl acetate/crotonic acid copolymers which are grafted onto polyethylene glycol, such as the product sold by the company HOECHST under the name "ARISTOFLEX A";

vinyl acetate/crotonic acid/vinyl neodecanoate terpolymers, such as the product sold under the name "RESYN 28-29-30" by the company NATIONAL STARCH;

polyacrylamides containing carboxylate groups, such as the product sold under the name "CYANAMER A 370" by the company AMERICAN CYANAMID.

The polymers containing sulfonic units are more particularly chosen from the sodium salts of polystyrenesulfonic acid, such as the products sold under the names "FLEXAN 500" and "FLEXAN 130", having a molecular weight of approximately 500,000 and 800,000 respectively, by the company NATIONAL STARCH.

salts of sulfonic polyacrylamides, such as polyacrylamidomethylpropanesulfonic acid, for instance the product sold under the name "COSMEDIA POLYMER HSP 1180" by the company HENKEL;

the salts of a polymer containing alkylnaphthalenesulfonic acid units, such as the product sold under the name "DARVAN No. 1" by the company VAN DER BILT;

sodium polyvinylsulfonates having a molecular weight of between 1,000 and 100,000.

Other anionic polymers such as the acrylamide/ammonium acrylate (5/95 by weight) crosslinked copolymer in a water-in-oil emulsion, sold by the company HOECHST under the name "BOZEPOL C", or the partially or totally neutralized acrylamide/2-acrylamido-2-methylpropanesulfonic acid crosslinked copolymer in an oil-in-water emulsion.

Nonionic treating agents may consist of nonionic polymers having a molecular weight between 500 and 3,000,000, which may be used alone or as a mixture with anionic and/or cationic polymers mentioned above.

Among these nonionic polymers, there may be mentioned:

polyvinylpyrrolidone, vinylpyrrolidone/vinyl acetate copolymers, polyacrylamides, polyethylene glycols, hydrophobic modified nonionic celluloses, such as the product sold under the name "NATROSOL Grade Plus 330 cs" by the company AQUALON, or under the name "AMERCEL HM 1500" by the company AMERCHOL, water-soluble polyamides, which are described more particularly in Patent U.S. Pat. No. 4,082,730 and in French Patent 2,508,795, and preferably poly-β-alanines.

Amphoteric polymers may also be used as treating agents, alone or in combination with the cationic derivatives or the polymers mentioned above. These polymers have a molecular weight of 500 to 3,000,000 and are chosen in particular from polymers containing A and B units distributed statistically in the polymer chain, where A denotes a unit derived from a monomer containing at least one basic nitrogen atom and B denotes a unit derived from an acidic monomer containing one or more carboxylic or sulfonic groups; A and/or B may also denote groups derived from zwitterionic carboxybetaine or sulfobetaine monomers.

A and B may also denote cationic polymer chains containing primary, secondary, tertiary or quaternary amine groups, in which one of the amine groups bears a carboxylic or sulfonic group which is attached by way of a hydrocarbon radical; or alternatively A and B form part of a polymer chain containing an α,β-dicarboxylic ethylene unit one of the carboxylic groups of which has been reacted with a polyamine containing one or more primary or secondary amine groups.

Particularly preferred amphoteric polymers are chosen from:

the polymers resulting from the reaction of a polyaminoamide obtained by polycondensation of adipic acid and diethylenetriamine in an equimolar amount and crosslinked with epichlorohydrin in a proportion of 11 moles of crosslinking agent per 100 secondary amine groups of the polyaminoamide, alkylated with propanesultone in proportions of 50% or alternatively with sodium chloroacetate;

the betainized polymer obtained by polycondensation of epichlorohydrin and piperazine in the presence of sodium hydroxide;

the copolymers of acrylic acid and of dimethyldiallylammonium chloride, sold under the names "MERQUAT 280" and "MERQUAT 295";

the octylacrylamide/acrylate/butylaminoethyl methacrylate copolymer sold under the name "AMPHOMER" by the company NATIONAL STARCH;

the methyl methacrylate/carboxymethyldimethylammo-nioethyl methacrylate copolymer;

($C_1$–$C_{18}$) alkyl methacrylate/carboxymethyldimethyl-ammoniomethyl methacrylate copolymers.

By way of example, there may be mentioned the product sold under the name "AMPHOSET" by the company MITSUBISHI PETROCHEMICAL Co., Ltd., or under the name weight of 70,000 to 90,000.

The chitosan-derived polymers described in particular in French Patent 2,137,684 result from the partial acylation of chitosan with a dicarboxylic acid.

By way of example, there may be mentioned the polymer containing 0 to 20% of acetylchitosan unit, 40 to 50% of chitosan unit and 40 to 50% of chitosan unit acylated with succinic acid.

The compositions in accordance with the invention may also contain non-cationic volatile or non-volatile silicones.

The volatile silicones possess a boiling point between 60 and 260° C. The non-volatile silicones are chosen more particularly from polyalkylsiloxanes, polyarylsiloxanes, polyalkylarylsiloxanes, polyether siloxane copolymers which may or may not be organically modified, silicone gums and resins, and organically modified polysiloxanes, as well as mixtures thereof.

The volatile silicones are chosen more particularly from cyclic silicones containing from 3 to 7 silicon atoms, such as octamethylcyclotetrasiloxane or decamethylcyclopentasiloxane, and cyclopolymers such as dimethylsiloxane/methylalkylsiloxane, or alternatively from linear volatile silicones having 3 to 9 silicon atoms, such as hexamethyldisiloxane.

The non-volatile silicones are chosen from:

a/ polyalkylsiloxanes, such as linear polydimethylsiloxanes containing terminal trimethylsilyl groups, having a viscosity of $5 \times 10^{-6}$ to 2.5 $m^2/s$. at 25° C., and linear polydimethylsiloxanes containing terminal trihydroxysilyl groups, and polyalkyl($C_1$–$C_{20}$)siloxanes;

b/ polyalkylarylsiloxanes chosen from linear and/or branched polydimethyldiphenylsiloxanes or polymethylphenylsiloxanes, having a viscosity of $10^{-5}$ to $5 \times 10^{-2}$ $m^2/s$. at 25° C.;

c/ modified or unmodified polyether siloxane copolymers;

d/ silicone gums consisting of polydiorganosiloxane with a high molecular weight of between 200,000 and 1,000,000, which are used alone or as a mixture with a solvent chosen from volatile silicones, polydimethylsiloxane (PDMS) oils, polyphenylmethylsiloxane (PPMS) oils, isoparaffins, methylene chloride, pentane, dodecane, tridecane, tetradecane or mixtures thereof;

e/ organopolysiloxane resins which have cross-linked siloxane systems containing $R_2SiO_{2/2}$, $RSiO_{3/2}$ and $SiO_{4/2}$ units, in which R represents a hydrocarbon group possessing from 1 to 6 carbon atoms or a phenyl group;

f/ the organically modified silicones defined above containing in the general structure thereof one or more organofunctional groups directly attached to the siloxane chain or attached by way of a hydrocarbon radical, chosen from:

(i) thiol groups,
(ii) carboxylate groups,
(iii) alkoxylated groups,
(iv) hydroxylated groups,
(v) acyloxyalkyl groups,
(vi) bisulfite groups.

These silicones are known per se or are among others described in greater detail in French Patent No. 2,653,016.

The organically modified silicones may also be chosen from silicones which are organically modified with polyethylenoxy and/or polypropylenoxy, alkylcarboxylic, 2-hydroxy-sulfonic, 2-hydroxyalkylthiosulfate and acylamidoalkyl groups.

The compositions in accordance with the invention may also contain isoparaffins or poly-α-olefins and perfluoro oils. There may be mentioned in this regard:

isoparaffins with a viscosity lower than 0.5 Pa.s, corresponding to the formula:

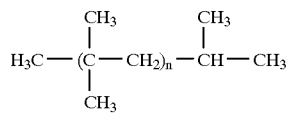

in which:

n is between 2 and 16 and the mixtures thereof with oils of identical structure, in which n is greater than 18, and preferably between 18 and 40; such oils are sold by the company PRESPERSE INC. under the names "PERMETHYL 99A, 101A, 102A, 104A and 106A", or by the company ICI under the name "ARLAMOL HD". The "ISOPARS" sold by the company EXXON INC. may also be mentioned.

hydrogenated or unhydrogenated poly-α-olefins of polydecene type; such products are sold by the company ETHYL CORPORATION under the name "ETHYLFLO". Hydrogenated or unhydrogenated polyisobutylenes are also mentioned.

perfluoro oils such as the perfluoropolymethylisopropyl ethers sold under the name "FOMBLIN" by the company MONTEFLUOS.

The cosmetic treating agents are present in the compositions in accordance with the invention in proportions which may range between 0.01 and 10% by weight relative to the total weight of the composition and preferably between 0.05 and 6% by weight.

When they are used in a treatment comprising a rinsing operation, these compositions may also contain electrolytes such as alkali metal salts, for example such as sodium, potassium or lithium salts.

These salts are preferably chosen from sulfates, halides such as the chloride or bromide or organic acid salts, in particular the acetate or lactate.

Alkaline-earth metal salts are also used, more particularly the calcium, magnesium or strontium carbonate, silicate, nitrate, acetate, gluconate, pantohenate [sic] or lactate.

These electrolytes are present in concentrations ranging between 0.25 and 8% by weight relative to the total weight of the composition.

The compositions in accordance with the invention may contain other active products, such as anti-greasy agents, anti-seborrheic agents, anti-dandruff agents, agents for combating hair loss or for promoting the regrowth of the hair, and anti-acne products.

The compositions may also contain other ingredients usually used in cosmetics, such as perfumes, dyes for the purpose of coloring the composition itself, the hair or the skin, preserving agents, sequestering agents, sunscreen agents and peptizing agents, optionally as well as anionic, nonionic or amphoteric surface-active agents or mixtures thereof, in proportions of less than 10% and preferably of less than 7%.

It is understood that when the active substances or the ingredients are present, they must not have a harmful effect on the production of the foam obtained by means of the vinyl lactam-derived terpolymer defined above.

The compositions in accordance with the invention are packaged in pressurized devices as an aerosol in the presence of the propellent gases which are generally present in proportions not exceeding 25% relative to the total weight of the composition, and preferably 15%.

By way of propellent gases, it is possible to use dimethyl ether, compressed air, carbon dioxide, nitrogen or nitrous oxide; volatile hydrocarbons such as butane, isobutane, propane and mixtures thereof; non-hydrolyzable chloro and/or fluoro halogenated hydrocarbons such as the compounds sold under the names "FREON" by the company DU PONT DE NEMOURS, and more particularly fluorochlorohydrocarbons such as dichlorodifluoromethane, Freon 12, or dichlorotetrafluoroethane, or Freon 114. These propellents may be used alone or as a mixture such as the mixture of Freon 114/Freon 12, in proportions of between 40:60 and 80:20.

The compositions introduced into the aerosol device, in accordance with the invention, may be in the form of a lotion, an emulsion or a dispersion which, after being dispensed from the aerosol device, form foams to be applied to the hair or to the skin.

The foams, dispensed from the aerosol devices, having the composition defined above may be applied in the form of a conditioner composition, a product to be rinsed which is to be applied before or after dyeing or bleaching, before or after permanent waving or hair straightening, as a hair setting or blow-drying agent or in the form of a product whose application is not followed by rinsing, such as styling mousses.

The foams in accordance with the invention are preferably used without their application being followed by rinsing.

These compositions may also be used for restructuring the hair, permanent waving or the dyeing and bleaching of the hair.

Their pH is generally between 3 and 10 and is adjusted using a basifying or acidifying agent which is commonly used in cosmetics.

When the foams in accordance with the invention are intended to be used for hair styling, hair shaping or hair setting, they generally comprise, in an aqueousalcoholic or aqueous dispersion or solution containing the vinyl lactam-derived terpolymer defined above, one or more cosmetic polymers as defined above.

When the foams in accordance with the invention are used for carrying out permanent waving, they contain, besides the vinyl lactam terpolymer defined above and cosmetic polymers, either a reducing agent or an oxidizing agent, depending on whether they constitute the first or the second phase of the permanent waving.

When the foam is applied to the skin, it contains various active adjuvants as defined above, depending on the intended application.

The examples which follow are intended to illustrate the invention without, however, being limiting in nature.

EXAMPLE 1

The following composition is prepared:

| | |
|---|---|
| Vinylpyrrolidone/acrylic acid/lauryl methacrylate terpolymer, sold under the name "ANIONIC VP TERPOLYMER" by the company ISP | 1g |
| Copolymer of vinyl methyl ether/maleic anhydride monoesterified with butanol, sold at an active substance (AS) concentration of 50% in ethanol, under the name "GANTREZ ES 425" by the company GAF | 1g |
| 2-Amino-2-methyl-1-propanol qs pH = 6.5 | |
| Oxyethylenated polydimethylsiloxane containing amide groups, sold under the name "SILWAX DCA-100" by the company SILTECH | 0.5g |
| Demineralized water qs | 100g |
| Aerosol packaging | |
| Above composition | 90g |
| Ternary mixture: butane/isobutane > 55%/propane, sold under the name "AEROGAZ 3.2N" by the company ELF-AQUITAINE | 10g |
| Total | 100g |

This composition is packaged in an aerosol device. After expansion into the air, it forms a stable foam with a creamy feel.

It is applied to the hair, and disappears after massaging in. The hair thus treated feels particularly soft and the hair style has good hold.

EXAMPLE 2

The following composition is prepared:

| | |
|---|---|
| Vinylpyrrolidone/acrylic acid/lauryl methacrylate terpolymer, sold under the name "ANIONIC VP TERPOLYMER" by the company ISP, 100% neutralized with 2-amino-2-methyl-1-propanol | 2g |
| | before neutralization |
| Quaternized polyvinylpyrrolidone copolymer having a Mw of 100,000, sold at an AS concentration of 50% under the name "GAFQUAT 734" by the company GAF | 0.5g AS |
| Quaternized soya protein hydrolyzate, sold as a 30% aqueous solution under the name "CROQUAT SOYA" by the company CRODA | 0.5g AS |
| Ethyl alcohol | 8.5g |
| Fragrance, preserving agent qs | |
| Demineralized water qs | 100g |
| Aerosol packaging | |
| Above composition | 85g |
| Ternary mixture: butane/isobutane > 55%/propane, sold under the name "AEROGAZ 3.2N" by the company ELF-AQUITAINE | 15g |
| Total | 100g |

This composition is used under the same conditions as that of Example 1. Similar results are obtained on the hair.

EXAMPLE 3

The following composition is prepared:

| | |
|---|---|
| Vinylpyrrolidone/acrylic acid/lauryl methacrylate terpolymer, sold under the name "ANIONIC VP TERPOLYMER" by the company ISP, 100% neutralized with 2-amino-2-methyl-1-propanol | 0.5g |
| | before neutralization |
| Hydroxyethylcellulose copolymer grafted via a radical route with diallyldimethyl-ammonium chloride, sold under the name "CELQUAT L200" by the company NATIONAL STARCH | 0.5g |
| Dimethylcetylhydroxyethylammonium chloride | 1g |
| Lactic acid qs pH = 5 | |
| Fragrance, preserving agent qs | |
| Demineralized water qs | 100g |
| Aerosol packaging | |
| Above composition | 90g |
| Ternary mixture: butane/isobutane > 55%/propane; sold under the name "AEROGAZ 3.2N" by the company ELF-AQUITAINE | 10g |
| Total | 100g |

After expulsion into the air, the composition packaged in an aerosol device forms a foam.

It is applied to pre-washed wet hair; after massaging in in order to work the foam into the hair, and leaving in place for 5 minutes, the hair is rinsed with water, dried and shaped. The dried hair is shiny, feels soft and has good hold over time. This foam may also be applied without performing a rinsing operation. Good softness and hold properties are observed.

EXAMPLE 4

The following composition is prepared:

| | |
|---|---|
| Vinylpyrrolidone/acrylic acid/lauryl methacrylate terpolymer, sold under the name "ANIONIC VP TERPOLYMER" by the company ISP | 1g |
| Copolymer of vinyl methyl ether/maleic anhydride monoesterified with butanol, sold at an active substance (AS) concentration of 50% in ethanol, under the name "GANTREZ ES 425" by the company GAF | 1g |
| 2-Amino-2-methyl-1-propanol qs pH = 6.3 | |
| Oxyethylenated polydimethylsiloxane, sold under the name "SILWET L7602" by the company UNION CARBIDE | 0.5g |
| Demineralized water qs | 100g |
| Aerosol packaging | |
| Above composition | 90g |
| Ternary mixture: butane/isobutane > 55%/propane, sold under the name "AEROGAZ 3.2N" by the company ELF-AQUITAINE | 10g |
| Total | 100g |

The foam obtained with this composition is used under the same conditions as in Example 1. The results are similar.

EXAMPLE 5

The following composition is prepared:

| | |
|---|---|
| Vinylpyrrolidone/acrylic acid/lauryl methacrylate terpolymer, sold under the name "ANIONIC VP TERPOLYMER" by the company ISP, 100% neutralized with 2-amino-2-methyl-1-propanol | 1.5g before neutralization |
| Methyl nicotinate | 0.1g |
| Fragrance, preserving agent qs | |
| Demineralized water qs | 100g |
| Aerosol packaging | |
| Above composition | 90g |
| Ternary mixture: butane/isobutane > 55%/propane, sold under the name "AEROGAZ 3.2N" by the company ELF-AQUITAINE | 10g |
| Total | 100g |

The foam obtained after expansion into the air from the aerosol device is used for treatment to counter hair loss.

It is applied to the hair and disappears after massaging in. It is observed that the treated hair feels soft and has good hold after styling.

After treatment for 2 months, a reduction in hair loss is observed.

I claim:

1. Aerosol device comprising an aerosol can having a valve for releasing contents of the aerosol can, the aerosol can containing foaming agent in a cosmetically acceptable aqueous medium for treating the skin or the hair, the foaming agent being capable of forming a foam after expansion into the air, the foaming agent consisting essentially of a terpolymer present in proportions of between 0.05 and 10% by weight consisting of 25 to 90% of vinyl lactam, 1 to 55% of unsaturated carboxylic acid and 1 to 20% of alkyl acrylate or methacrylate containing at least 6 carbon atoms.

2. Device according to claim 1, wherein the unsaturated carboxylic acid is acrylic acid, methacrylic acid, itaconic acid or crotonic acid.

3. Device according to claim 1, wherein the vinyl lactam is 2-vinylpyrrolidone.

4. Device according to claim 1, wherein the acrylic or methacrylic esters contain 8 to 18 carbon atoms.

5. Device according to claim 4, wherein the alkyl radicals of the acrylic or methacrylic esters are 2-ethylhexyl, octyl, lauryl or stearyl radicals.

6. Composition intended for treating the hair or the skin, and intended to be packaged in a pressurized device as an aerosol in the presence of a propellent, consisting essentially of, in a cosmetically acceptable aqueous medium, at least one terpolymer present in proportions of between 0.05 and 10% by weight consisting of 25 to 90% of vinyl lactam, 1 to 55% by weight of unsaturated carboxylic acid and 1 to 20% of alkyl acrylate or methacrylate containing at least 6 carbon atoms which, after expansion, forms a foam.

7. Composition according to claim 6, wherein the unsaturated carboxylic acid is acrylic acid, methacrylic acid, itaconic acid or crotonic acid.

8. Composition according to claim 6, wherein the aqueous cosmetic medium contains water or a mixture of water and a cosmetically acceptable solvent present in an amount of less than or equal to 50% by weight relative to the total weight of the composition to obtain with the vinyl lactam terpolymer a foam having a density of less than or equal to $0.3 g/cm^2$ at 20° C. and having a stability of greater than 5 minutes.

9. Composition according to claim 6, which it contains treating agents which are cationic surface-active agents, cationic polymers, anionic polymers, nonionic polymers or amphoteric polymers.

10. Composition according to claim 5, which contains volatile or non-volatile silicones which are polyalkylsiloxanes, polyarylsiloxanes, polyalkylarylsiloxanes, or silicones which are organically modified with polyethylenoxy, polypropylenoxy, thiol, carboxylate, alkoxy, hydroxyl, acyloxyalkyl, alkylcarboxylic, 2-hydroxysulfonic, 2-hydroxyalkylthiosulfate or acylamidoalkyl groups.

11. Composition according to claim 5, which additionally contains an isoparaffin, a poly-α-olefin or a perfluoro oil.

12. Composition according to claim 6, wherein the vinyl lactam polymer is present in proportions of between 0.05 and 10% by weight relative to the total weight of the composition.

13. Composition according to claim 6, which composition contains a treating agent which is present in proportions of between 0.01 and 10% by weight relative to the total weight of the composition.

14. Composition according to claim 6, which contains electrolytes which are sulfates, halides or organic acid salts of alkali metals or of alkaline-earth metals.

15. Composition according to claim 6, which contains cosmetic or dermatological active agents.

16. Composition according to claim 6, wherein the active agents are anti-greasy agents, anti-seborrheic agents, anti-dandruff agents, anti-acne agents, products for combating hair loss or for promoting the regrowth of the hair.

17. Composition according to claim 6, which also contains fragrances, dyes for the purpose of coloring the composition itself or the hair or the skin, preserving agents, sequestering agents, emollients, sunscreen agents or peptizing agents.

18. Composition according to claim 6, which also contains anionic, nonionic or amphoteric surface-active agents or mixtures thereof, in proportions not exceeding 10%.

19. Composition according to claim 6, which is applied in the form of a conditioner composition, a foam to be rinsed, a hair setting foam, a blow-drying foam, a foam which is not rinsed out after application, a restructuring composition, a permanent-waving composition, a dyeing composition or a bleaching composition.

20. Process for the cosmetic treatment of the hair or of the skin, comprising applying at least one foam resulting from the expansion into the air of the composition as defined in claim 6 to the skin or to the hair, this application optionally being followed by a rinsing operation.

21. Composition according to claim 6 intended for the therapeutic treatment of the skin, which contains at least one dermatologically active substance.

22. Composition according to claim 6, wherein the vinyl lactam polymer is present in proportions of between 0.2 and 3% by weight relative to the total weight of the composition.

23. Device according to claim 1, wherein the cosmetically acceptable aqueous medium contains water or a mixture of water and a cosmetically acceptable solvent present in an amount to permit obtaining a foam.

24. Composition according to claim 6, wherein the cosmetically acceptable aqueous medium contains water or a mixture of water and a cosmetically acceptable solvent present in an amount to permit obtaining a foam.

* * * * *